United States Patent
Sung

(10) Patent No.: US 10,258,326 B2
(45) Date of Patent: Apr. 16, 2019

(54) ELASTIC TISSUE REINFORCING FASTENER

(71) Applicant: Ethicon, Inc., Somerville, NJ (US)

(72) Inventor: An-Min Jason Sung, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 270 days.

(21) Appl. No.: 15/018,405

(22) Filed: Feb. 8, 2016

(65) Prior Publication Data

US 2017/0224338 A1  Aug. 10, 2017

(51) Int. Cl.
*A61B 17/06* (2006.01)
*A61B 17/00* (2006.01)

(52) U.S. Cl.
CPC .......... *A61B 17/06166* (2013.01); *A61B 2017/00862* (2013.01); *A61B 2017/0618* (2013.01); *A61B 2017/06176* (2013.01); *A61B 2017/06185* (2013.01)

(58) Field of Classification Search
CPC .......... A61B 17/0401; A61B 17/0469; A61B 17/06166; A61B 17/0618; A61B 2017/06052; A61B 2017/06057; A61B 2017/06176; A61B 2017/06185
See application file for complete search history.

(56) References Cited

U.S. PATENT DOCUMENTS

| | | | |
|---|---|---|---|
| 3,123,077 A | 3/1964 | Alcamo | |
| 3,875,928 A | 4/1975 | Angelchik | |
| 4,271,828 A | 6/1981 | Angelchik | |
| 5,006,106 A | 4/1991 | Angelchik | |
| 5,972,022 A | 10/1999 | Huxel | |
| 6,241,747 B1 | 6/2001 | Ruff | |
| 6,592,596 B1 | 7/2003 | Geitz et al. | |
| 6,848,152 B2 | 2/2005 | Genova et al. | |
| 6,960,233 B1 | 11/2005 | Berg et al. | |
| 7,011,622 B2 | 3/2006 | Kuyava et al. | |
| 7,226,468 B2 | 6/2007 | Ruff | |
| 7,326,172 B2 | 2/2008 | Miller | |
| 7,445,010 B2 | 11/2008 | Kugler et al. | |
| 7,695,427 B2 | 4/2010 | Kugler et al. | |
| 7,942,887 B2 | 5/2011 | Kraemer et al. | |
| 8,747,436 B2 | 6/2014 | Nawrocki et al. | |
| 8,795,332 B2 | 8/2014 | Leung et al. | |
| 2005/0267531 A1 | 12/2005 | Ruff et al. | |
| 2006/0121274 A1 | 6/2006 | Capurro | |
| 2007/0005110 A1 | 1/2007 | Collier et al. | |
| 2008/0046094 A1 | 2/2008 | Han et al. | |
| 2008/0221618 A1 | 9/2008 | Chen et al. | |

(Continued)

FOREIGN PATENT DOCUMENTS

EP 0 664 198 A1 7/1995
WO WO 2015/171962 A1 11/2015

OTHER PUBLICATIONS

Collins, C D, H L Duthie, T Shelley, and G E Whittaker "Force in the anal canal and anal continence" Gut, 1967, 8, 354-360.

(Continued)

*Primary Examiner* — Robert A Lynch
(74) *Attorney, Agent, or Firm* — Frost Brown Todd LLC

(57) ABSTRACT

A tissue fastener having fixed points of tissue attachment including a first elongate elastic component and a second elongate component having one or more elongate sections each adjacent section delineated by at least one frangible point.

20 Claims, 2 Drawing Sheets

(56) References Cited

U.S. PATENT DOCUMENTS

| | | |
|---|---|---|
| 2009/0248066 A1 | 10/2009 | Wilkie |
| 2009/0259252 A1 | 10/2009 | Kennedy et al. |
| 2010/0160961 A1 | 6/2010 | Nawrocki et al. |
| 2011/0251640 A1 | 10/2011 | Lauria |
| 2012/0109193 A1 | 5/2012 | Primavera et al. |
| 2012/0136388 A1 | 5/2012 | Odermatt et al. |
| 2013/0226233 A1* | 8/2013 | D'Agostino ............ A61B 17/04 606/228 |
| 2015/0157308 A1* | 6/2015 | Sengun .............. A61B 17/0485 606/148 |

OTHER PUBLICATIONS

Noar, Mark D "Chronic Faecal Incontinence—Review of the Disease State, Therapeutic Alternatives and Algorithmic Approach to Treatment—Chronic Faecal Incontinence—A Review" TouchGastroenterology.com, Nov. 2011.

European Search Report and Written Opinion dated Apr. 18, 2017 for Application No. EP 17155047.8, 9 pgs.

International Search Report and Written Opinion dated May 3, 2017 for Application No. PCT/US2017/015761, 16 pgs.

* cited by examiner

ELASTIC TISSUE REINFORCING FASTENER

FIELD

The device described herein is an implantable suture device that provides sufficient retention in tissue, while also providing elasticity and axial stretch.

BACKGROUND

Sutures having fixed points of attachment to tissue, such as retainers (or "barbs"), do not typically enable tissue to stretch. Such self-retaining sutures are secured into the tissue by embedding the retainers into a portion of the tissue, thereby holding the suture along its barbed length securely in tissue. While this may be acceptable for many surgical applications, as the retainers maintain the suture in its implanted position without the need for additional anchors, it may not be preferable for certain applications. In some procedures, the implanted suture could benefit from the ability to stretch along the length of the suture. Such procedures include, for example, those used to retain surgical mesh in place, suturing of sphincters or other bodily orifices that functionally expand and contract, and in applications where the sutured tissue is expected to grow (e.g., when used in patients who are not fully grown).

While self-retaining sutures themselves are known, present sutures are limited. The main application for sutures, such as barbed sutures, currently is to approximate and close tissue gaps, where the gap is intended to remain closed and there is little desire to stretch and move. This is the precise reason that many self-retaining sutures are not intended to "give" under low stresses (such as less than about 0.5 lb). If the suture does give under this level of stress, it would be considered by many to be a failure and may not achieve its intended purpose. This is especially true when used in closing a surgical wound for healing. Although there are various designs known, none has demonstrated the ability to elongate at a significant displacement (greater than 5 mm) under non-catastrophic stresses and return to its original state when stresses are removed. There is a need for sutures, including self-retaining sutures, to allow for stretching and flexibility after implantation.

SUMMARY

In one aspect, the present invention may include a tissue fastener having fixed points of tissue attachment including a first elongate elastic component; and a second elongate component having one or more elongate sections each adjacent section delineated by at least one frangible point; where each elongate section has one or more tissue anchoring elements, and the elasticity of the first elongate component is greater than that of the second elongate component.

The present invention also includes a method of applying the aforementioned tissue fastener to tissue repair in surgical procedures associated with any of the following: prolapsed pelvic floor, sphincters, gastroesophageal reflux disease (GERD), fundoplication, fecal incontinence, lung volume reduction, myocardial tissue stress reduction, or any tubular structure required reinforcement where the tubular structure may need to open elastically for bodily function.

In another aspect of the invention, there is a tissue fastener having fixed points of tissue attachment including: a first elongate elastic component and a second elongate elastic component; a third elongate component having one or more elongate sections adjacent to each other, each elongate section being disposed between the first and second elongate elastic component; where each elongate section has one or more tissue anchoring elements, and the elasticity of each of the elastic elongate components is greater than that of the third elongate component.

There are also provided methods of making and using the tissue fastener described herein.

DETAILED DESCRIPTION

Figure 1:
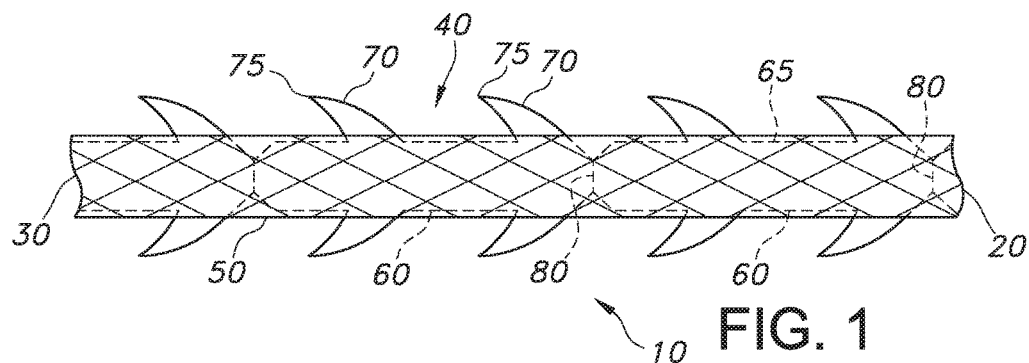
FIG. 1 depicts one embodiment of a composite suture device including a braided outer sheath.

As used herein, the term "suture" will refer generally to a tissue fastening device that includes an elongated thread or wire used to treat or repair tissue. Sutures may be monofilament or multifilament, and may have any desired length. Suture strands may have any cross sectional configuration, including triangular, circular, square, or other shape, and have a central axis running from first end to second end. Unidirectional sutures are those that include an insertion device (e.g., a needle or pointed end) at one end of the suture, and are intended to be implanted by inserting the insertion device into tissue and pulling the suture a desired length. The unidirectional suture may have an end effector or other anchoring device at its opposite end, designed to stop the movement of the suture through tissue. Bidirectional sutures are those that include an insertion device at each end of the suture, and can be implanted in either or both ends by inserting the insertion devices through tissue. Multidirectional sutures may include any number of suture strands emanating from a central point, and may include, for example, three or more sutures, each with free insertion ends (which may have insertion devices thereon). Unless used otherwise, the term "suture" may refer to any of the aforementioned types of sutures.

Self-Retaining sutures are those that include retainers on or along at least a portion of the axial length, where the retainers are sized sand shaped to engage a portion of tissue during and after insertion, holding the suture in place in tissue. For example, self-retaining sutures may have a series of barbs or pointed features along a portion of the axial length, such as described in U.S. Pat. No. 6,848,152, the entire contents of which are incorporated by reference herein. Retainers (or barbs) may be formed by cutting into the suture body, or may be disposed on the outer surface of the suture. Retainers may lie flat until a force extends the pointed end of the retainer out, or retainers may extend outward from the suture body in the absence of force.

Retainers should be configured so as to allow for the suture to be pulled through tissue in a first direction, but once implanted, resist movement in a second, opposite direction. Other non-limiting exemplary self-retaining suture configurations include those described in U.S. Patent Publication No. 2005/0267531 and in U.S. Pat. No. 8,795,332, each of which are incorporated by reference herein in their entireties.

Sutures, including self-retaining sutures, are generally made from materials that are flexible and capable of being bent and curved by a user during implantation. Suitable materials are described in further detail below. However, as can be understood by those of skill in the art, when self-retaining sutures are implanted, the ability of the suture to flex and expand is limited due to the tissue engagement by retainers, and in many instances, the suture (and therefore the tissue into which the suture is implanted) is restricted from being flexed or expanded after implantation.

Despite the benefit of a self-retaining suture to be secured effectively in tissue, the ability for a surgical fastener to expand, stretch and recover is critical to some surgical procedures for tissue repair and/or reinforcement. Non-limiting diseases such as pelvic floor prolapse, gastroesophageal reflux disease (GERD), and fecal incontinence (FI) involve the loss of elasticity of tissues due to one reason or another therefore lost their functionalities. The standard of care for pelvic floor repair surgery involves the use of a mesh implant, which may result in ingrowth of scar tissue that has minimum elasticity. On the other hand, the surgery for either GERD or FI also does not restore the elasticity of tissue. In these and other procedures, it would be useful to have a suture that, after implanted, has the ability to expand and stretch, which therefore allows the tissue into which it is implanted to expand and stretch.

Previous attempts to create an elastic self-retaining suture have relied upon, for example, the use of separately attached barbed rings secured to the suture strand or coiled regions of suture material (U.S. 2009/0248066), or an elastic core surrounded by a coiled non-elastic sheath (U.S. 2006/0121274). The present invention seeks to provide a suture, which may be a self-retaining suture, which provides for tissue fastening and attachment while allowing for a natural degree of elasticity. As used herein, the term "elastic" refers to the ability of the suture device to be axially expanded such that its expanded axial length is greater than its axial length prior to expansion. An elastic suture is useful in repairing or treating tissue that requires the tissue have some degree of elasticity after a suture is implanted into the tissue. Degrees of elasticity will be described in greater detail below.

The present embodiments described herein are useful in that they are capable of providing support or reinforcement to weakened tissues with tissue fastening devices having fixed points of tissue attachment, while also allowing for a natural degree of elasticity. Examples of fasteners related to this invention include, for example, meshes or rigid (or semi-rigid) stiffeners, and self-retaining sutures. One embodiment of the invention is a composite structure having a barbed core with elastic sheath as shown in FIG. 1. The embodiment of FIG. 1 is beneficial in that it incorporates a plurality of built-in frangible points within the barbed core, which can be strategically severed based on the need for tissue extension between anchoring points. Frangible points are seen in greater detail, for example, in FIG. 2.

It may be useful for the aforementioned configuration to include an elastic sheath made from elastic material, such as a braided elastic fiber(s) or an elastic film. Where an elastic film is used, the film may optionally have apertures to expose the frangible points of the barbed core for easy access and breaking. The elastic sheath remains over the core, allowing the retainers (barbs) of the core to engage tissue while the elastic sheath allows for the fastener to elongate as needed. Since the elastic sheath remains intact, the suture device is not severed, and it is capable of keeping a hold on the tissue into which it is implanted. That is, only the desired points in the core are severed, but the outer body of the suture device is kept intact. This allows for expansion and stretching of the suture device, since the inner core portions are capable of being separated from each other at the frangible points.

This embodiment will now be described in greater detail, with reference to the Figures.

FIG. 1 depicts one embodiment of the present invention, which includes an inner core with retainers and an outer sheath. The suture device 10 is a generally elongated device, having a first end 20, a second end 30 and an elongated body 40. The device 10 may have any desired cross section, and in some embodiments it may have a generally circular cross section, while in other embodiments, it may be square or rectangular in cross section. The device 10 includes an outer sheath 50, which is seen as a braided component, but it may be understood that the sheath 50 can have alternative configurations, including a film. It is particularly desired that the sheath 50 be flexible and expandable in an axial direction. That is, the sheath 50 should be capable of being stretched in a direction facing either or both of the first end 20 and/or second end 30, thereby increasing its axial length as measured from first end 20 to second end 30 when stretched.

The degree of stretching and elasticity may vary depending upon the intended use and the tissue into which the device is to be inserted. In some embodiments, the degree of elastic stretch (in the axial direction) under physiological conditions is about 20% or greater, for a device having an axial length of at least 2.5 cm. In some embodiments, the axial stretch may be about 15% or greater, or may be about 30% or greater. The force required to cause axial stretching may be from about 1 gram of force to about 10 grams of force, or up to about 20 grams of force. In some aspects, the "spring modulus" of the device may be greater than about 2 g/cm, and may be greater than about 5 g/cm, and may be greater than about 10 g/cm.

The device 10 includes a plurality of retainer segments 60, which are elongated and housed within the sheath 50. In some embodiments, there may be two retainer segments 60, in others there may be three or more retainer segments 60. For example, one suture device 10 may have from about 5 to about 50 retainer segments 60, or about 40 retainer segments 60, or about 30 retainer segments 60, or about 20 retainer segments 60. The retainer segment 60 has an elongated segment body 65, with at least one retainer 70 extending outward from the sides of the segment body 65. Desirably, each retainer segment 60 has at least two, or at least four retainers 70 extending outward from the segment body 65. Each retainer 70 may have a pointed tip 75, or an alternative tissue-engaging feature at its tip 75.

The segment body 65 is substantially housed within the sheath 50, such that the retainer segment 60 is axially aligned with the sheath 50, forming a coaxial arrangement. At least one retainer 70, and desirably each retainer 70 in the retainer segment 60 extends through the sheath 50, such that the tissue engaging tip 75 is exposed through the outer circumference of the device 10. Each retainer 70 is aligned so that the tip 75 faces a direction towards either the first end 20 or the second end 30 of the device 10, which allows insertion of the device 10 through tissue, but restricts movement of the device 10 in the opposite direction after inserted into tissue. In a unidirectional device, each retainer 70 is aligned such that each tip 75 faces in a direction opposite the insertion end (or needled end, if a needle is secured to one end of the device 10). For a bidirectional device, each end of the device (first end 20, second end 30) is an insertion end, which may include a needle or other insertion device. In such embodiments, there are two series of retainers 70, a first set of retainers proximal to the first end 20, and a second set of retainers proximal to the second end 30, with an intervening location between the first and second sets of retainers. The first set of retainers is each aligned such that each tip 75 faces in a direction opposite the first end 20. Conversely, the second set of retainers is each aligned such that each tip 75 faces in a direction opposite the second end 30. The intervening location may be free of retainers and may be any size desired. The bidirectional device allows insertion by both the first end and second end, while providing tissue retention due to the alignment of the first and second sets of retainers.

The retainers 70 should each be sufficiently flexible such that the retainers 70 can be compressed towards the body 40 of the device when inserted into tissue, allowing the device 10 to be pulled through tissue without significant restriction or damage to the tissue. In some embodiments, the retainers 70 lie substantially flat during insertion, where the tips 75 are not extended outward until and unless force is acted thereon. In other embodiments, the tips 75 extend outward but are capable of being pushed towards the axial center of the suture body during insertion.

Figure 2:
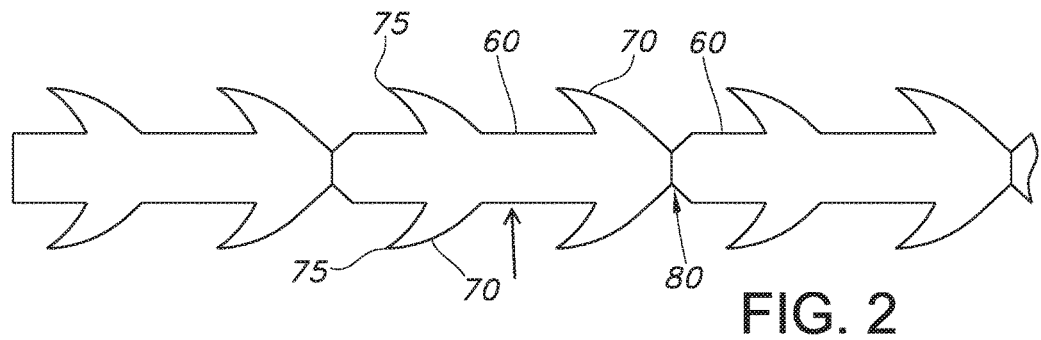
FIG. 2 depicts a close up view of the retainer segments of a suture core.

As noted above, the device 10 includes at least two retainer segments 60 within the sheath. Each retainer segment 60 is secured to another retainer segment 60 at an end, where the securement of retainer segments 60 is frangible, forming a frangible point 80. The frangible points 80 are housed within the sheath 50. FIG. 2 shows a possible configuration for the retainer segments 60, where the sheath 50 has been removed. As can be seen, each retainer segment 60 has a segment body 65 with a plurality of retainers 70 extending outward from the body 65. The retainer segments 60 are in contact with at least one retainer segment 60 at a frangible point 80.

Frangible point 80 may be formed through any desired means. As an example, frangible point 80 can be created by a compression-die after elongated segment body is made through either extrusion or injection molding. The compression-die creates notches as weaken points between retainer segments at a pre-determined or desired length. Or, alternatively, the frangible point can be created during molding process. During surgical procedure the frangible point can then be broken by stretching two sides of the selected frangible point with graspers holding two sides.

The device 10 may include a needle or other insertion device (not shown) at either or both of the first end 20 and/or second end 30, depending upon whether the device is a unidirectional or bidirectional device. If an insertion device is included only at a first end 20, the second end 30 may optionally include an anchor or other end effector to provide a means to stop the device 10 from being pulled entirely through the tissue into which it is placed. The end effector may be a knot, or a loop, or a bar, or a clip, or a button, or any other device having an increased size with respect to the circumference of the device 10, serving as an anchor for the device 10.

In use, the device 10 may be bent or flexed to allow for insertion into tissue. Any or all of the frangible points 80 may be broken, either prior to insertion or during insertion through tissue. When the frangible point 80 between any two retainer segments 60 is broken or severed, the adjacent retainer segments 60 are free to be axially separated from each other. Since the sheath 50 is expandable and stretchable in an axial direction, expansion of the sheath axially separates the retainer segments 60 from each other, thereby increasing the overall axial length of the device 10 as measured from first end 20 to second end 30. As can be appreciated, as more frangible points 80 are severed, the ability of the device 10 to stretch axially is increased, since more retainer segments 60 are movable with respect to each other. As more retainer segments 60 are separated from each other, the sheath 50 is able to more freely stretch axially without hindrance or restriction.

Since the device 10 is capable of being axially stretched, while still being held in place within tissue (by the retainers 70), the device 10 can effectively hold tissue together while allowing flexibility and stretching if necessary. For tissue that is required to expand and contract for bodily function, the present device 10 allows for tissue security and expansion. This ability to expand and contract while holding tissue together is an improvement over prior devices which are effective at holding tissue together, but are not or are less effective in allowing stretching of tissue after implantation.

Each retainer segment may be any desired size and have any number of retainers 70 thereon. In some embodiments, the retainer segments each include the same number of retainers, and in other embodiments, retainer segments may have different numbers of retainers. In some embodiments, one segment 60 will include at least three retainers 70 spaced around the body 65, or may include at least five retainers 70 spaced around the body. Retainers may be located in a linear fashion along the axis of the suture, or may be randomly spaced about the body 65.

Each retainer 70 may be sized and shaped for the intended purpose, and with consideration of the tissue into which it is to be inserted. Retainers may have a size of from about 0.001" to about 0.004", as measured from the base to tip 75, where the base is defined as the intersection of the underside of the retainer and the retainer segment body. The size of retainer 70 may vary, and will depend on the desired shape and method of forming the retainer. With minimum of about 0.001" can ensure the engagement of tip 75 with tissue. The sheath may have any desired axial size, and may have any desired cross-sectional sizing and shape. A sheath may have an axial length of from about 1" to as long as about 18", and in embodiments where a sheath has a circular cross-section, the sheath may have a cross-sectional diameter of about 0.004", as measured from the internal side walls across a diameter. The cross-sectional diameter of the sheath, as measured from the outer surface across its diameter to the opposing outer surface may be from about 0.004" to 0.018" or longer as desired. It is desired that the sheath have an axial length that is at least as long as or longer than the length of the retainer segments to be used as measured from end-to-end. The retainer segments should be housed within the sheath in this configuration.

The sheath may be sized and shaped to provide a desired overall length of the suture device. The overall length of the suture device, including sheath and retainer segments, may be from about 1" to 18" or longer as desired, as measured from first end 20 to second end 30. The device may include a plurality of retainers, and may include a plurality of retainer segments, each with a frangible point separating adjacent retainer segments.

Figure 3:
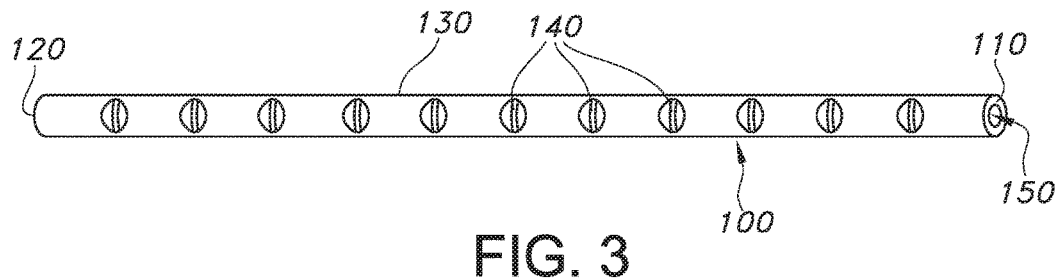
FIG. 3 depicts an embodiment of an elastic film sheath.

FIG. 3 depicts an alternate embodiment of a sheath useful in the present invention. As depicted in FIG. 3, the sheath may be a film-like material, as opposed to a braided configuration as described above. The sheath 100 is a generally elongated device, having a first end 110 and second end 120, with body 130 extending axially therebetween. The body 130 of the sheath 100 includes a plurality of openings 140 along its length, which are individually sized and shaped to allow for a retainer to extend through the opening 140. The sheath 100 has an open interior 150 extending from first end 110 to second end 120, which is shaped and sized to house a core. The cross-section of the sheath 100 may be circular, as shown in the Figure, but may be square, rectangular, diamond, oval, or any other desired shape.

The sheath 100 is desirably made from an expandable and stretchable material, where the sheath 100 can extend axially between the first end 110 and second end 120, thereby increasing its axial length when stretched. It is desirable that the sheath 100 be flexible, allowing bending of the sheath 100 during use. Suitable materials for the sheath 100 include, for example, silicone or polyurethane, or other similar biocompatible and elastic materials, including thermoplastic elastomers, such as TEO, SEBS, TPV, TPU, COPE, PEBA, and mixtures thereof. Suitable materials for the retainer segments 70 include, for example, olefins (such as LDPE, HDPE, LLDPE, UHMPE, PP), nylons, PVDF, PGA, PLA, PLGA, PDS, and combinations of such materials.

Figure 4:
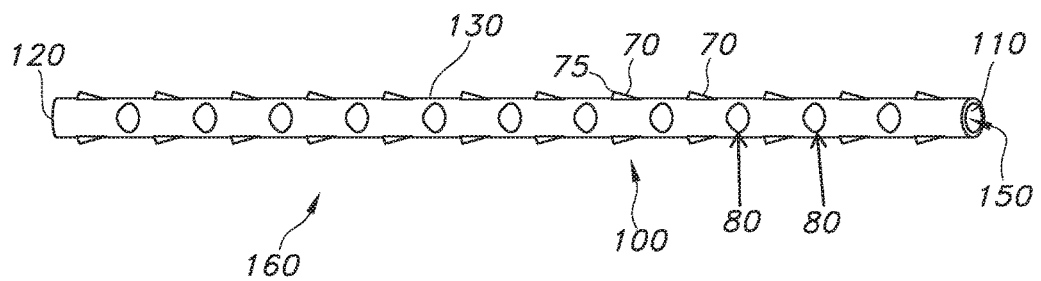
FIG. 4 depicts a composite suture device including a film sheath.

FIG. 4 depicts a self-retaining suture device 160, which is a composite device including the sheath 100 of FIG. 3 with a plurality of retainer segments 60 housed within the open interior 150. As can be seen, the sheath 100 includes retainer segments 60 within its interior 150, where the retainers 70 extend outwardly through the openings 140 in the body 130. It is desired that only one retainer 70 extend through each opening 140 in the sheath body 130, and that the retainer 70 be snugly fit within the opening 140. The number of openings 140 in the sheath body 130 should be equal to the number of retainers 70 to be included in the device 160. This configuration can best be seen in FIG. 5, which is a close-up of one segment of the composite suture device 160. As can be seen, the retainers 70 face with their respective tips 75 facing the second end 120. Therefore, in this Figure, the first end 110 is the insertion end, and may include an insertion device, such as a needle, secured thereto to allow penetration into and through tissue. The second end 120 may optionally include an anchor or end effector, as described above.

Figure 5:
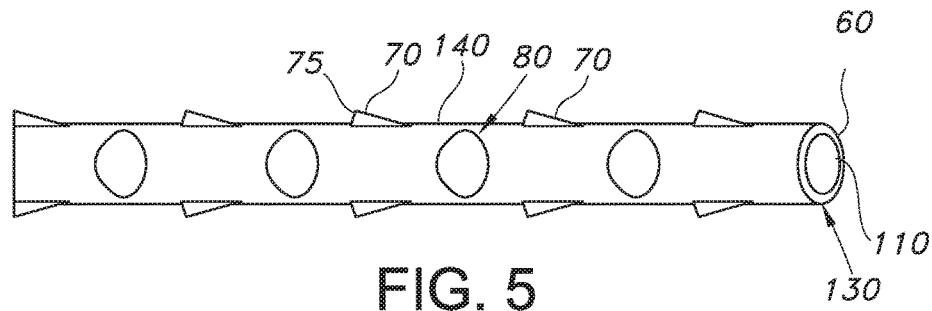
FIG. 5 is a close up view of a section of the device of FIG. 4.

FIGS. 4 and 5 show the sheath 100 including openings 140 aligned with the frangible points 80 between adjacent retainer segments 60. The sheath 100 may include openings 140 or fenestrations aligned with frangible points 80, so that a user can more clearly determine the breaking point between retainer segments 60, but these openings 140 are not required in the final device 160. That is, the composite device 160 may only include openings 140 aligned with retainers 70, such that the retainers 70 can extend through the sheath 100, and there may be no openings 140 at the frangible points 80. The sheath 100 may optionally include markings or other indicia aligned with frangible points 80 to allow a user to quickly determine where the frangible points 80 are located. Alternatively, there may be no marking or other feature to allow a user to determine the location of frangible points 80, and a user may simply exert force where desired to sever or break the nearest frangible point or points 80. For example, a user may bend the suture device 160 where desired to sever a frangible point 80, or may pull on the device 160 axially in one or both directions to break frangible point(s) 80. Breaking of frangible points 80 may occur before implantation in tissue or after implantation in tissue, or alternatively, during implantation of the device 160.

As described above, with a frangible point 80 broken, adjacent retainer segments 60 are capable of being moved axially away from each other, thereby freeing the ability of the sheath 100 to expand axially. As the sheath 100 expands axially, a first retainer segment 60 (and its associated retainers 70) is capable of being moved in the expanded direction, separating itself from the adjacent retainer segment 60. This allows the overall device 160 to increase its axial length while maintaining the retainers 70 in the required position to engage tissue.

The device described above may be made through any desired manufacturing methods. In one embodiment, the device may be made by a two-stage injection molding process. The first stage forms the core, which includes the plurality of retainer segments 70, by injecting a biocompatible and desired material into a mold or cavity. The frangible points 80 may be included in the mold, thereby allowing the injection molded device to include the retainer segments 70 and frangible points 80 in the same molded product. In another embodiment, the device may be made by a first step of first extruding the elongated retainer segment and then a second step to create the retainer(s) 70 and frangible point(s) 80, followed by a third step of extruding or molding or braiding over with an elastic sheath.

In use, a user may select a suitable composite device, which includes the elastic sheath with retainers therein, each retainer being adjoined to an adjacent retainer by a frangible point, as described above. The device may include a needled end or needled ends. The user may break one or more frangible points prior to insertion into tissue, or may break frangible points after insertion into tissue. As described above, breakage of frangible points may be achieved by subjecting the space between adjacent retainer segments to force sufficient to separate the segments. Force may be achieved by pulling the device axially, or by bending the device at the desired location or locations to cause site specific breaking. In embodiments where the user breaks one or more frangible points prior to insertion, the user will break the desired number of frangible points, and then proceed to insert the device into tissue by inserting the first end (insertion end) into tissue to a desired length. The user may then insert the device into another region of tissue, continuing to insert the device repeatedly until suturing is complete. As the device is inserted, the tissue retainers engage tissue, holding the device in place in the tissue into which it is implanted. In some embodiments, such as those described with respect to FIG. 6 below, the device may already include separated retainer segments, which do not need to be broken to separate the retainer segments.

Once suturing is complete, the retainers continue to hold that retainer segment and therefore the associated region of the suture sheath, in place. When tissue is allowed to stretch or move, the sheath at the region of stretching also stretches, causing separation between adjacent retainer segments, which have already been broken at the frangible point therebetween. The ability of the sheath to stretch at broken points allows tissue to expand and contract, while still remaining held in tissue by the retainers.

Non-limiting suitable tissues into which the device may be implanted include, for example, those tissues associated with repair in surgical procedures associated with any of the following: prolapsed pelvic floor, sphincters, gastroesophageal reflux disease (GERD), fundoplication, fecal incontinence, lung volume reduction, myocardial tissue stress reduction, or any tubular structure required reinforcement where the tubular structure may need to open elastically for bodily function. In addition, sutures of the present invention are useful for implantation into individuals who have not yet fully grown, including children.

Figure 6:
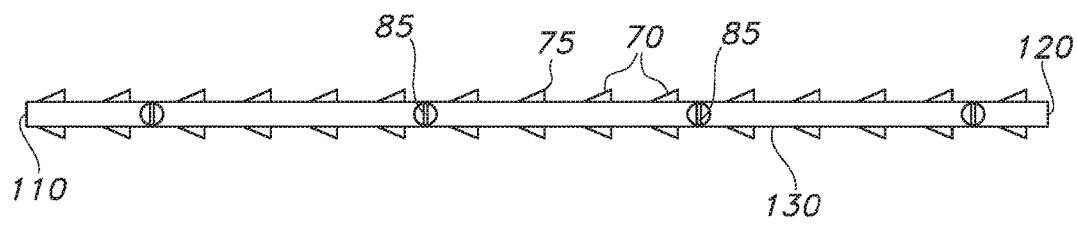
FIG. 6 depicts an alternate design where the device includes spaced barbed segments.

FIG. 6 depicts an alternate configuration of the designs described above, where the retainer segments 70 are separated by spaced-apart segments 85, instead of frangible points. Such a configuration is useful in situations where a user would need a ready-made device, with retainer segments already broken and separated. Thus, in the embodiment described in FIG. 6, the device is capable of being axially stretched without the need for breaking anything holding retainer segments together. The illustration in FIG. 6 shows an opening where one may visually see the spaced apart sections 85, but it is understood that openings are not necessary and in some instances, may be undesired.

Figure 7:
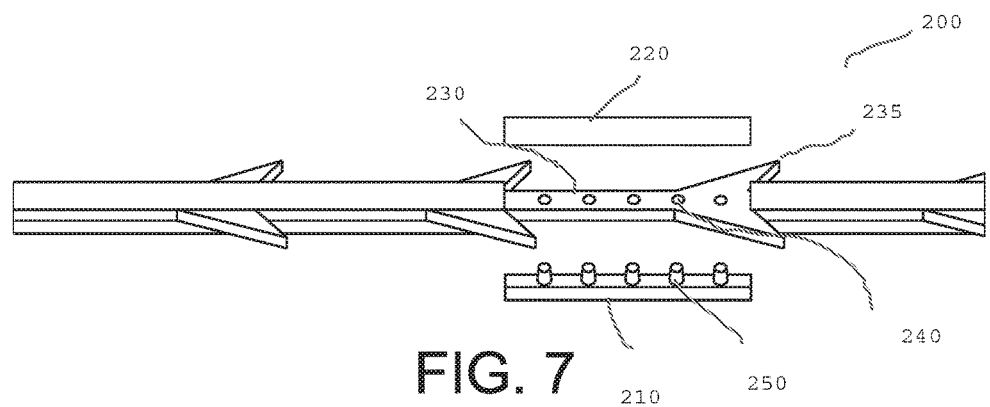
FIG. 7 depicts an embodiment where elongate elastic components are fixed to one another through openings in a non-extendible tissue engaging component.

In an alternate embodiment, as seen in FIG. 7, a device 200 is made with a first elongate elastic component 210 and a second elongate elastic component 220 sandwiching a non-extendible tissue engaging component 230. The non-extendible tissue engaging component 230 may include at least two outwardly extending retainers 235, which include a tissue engaging element, such as a pointed end. The sandwiching may be made through a series of openings 240 in the tissue engaging component 230 and insertion posts 250 extending from the first elongate elastic component 210. Second elongate elastic component 220 may include a series of receiving bores or other attachment sites (not shown) into which the insertion posts 250 may be secured. The device includes a plurality of sandwiched non-extensible tissue engaging components 230, which are secured to an adjacent sandwiched non-extensible tissue engaging component 230 via a frangible point as previously described. Selected or all adjacent non-extensible tissue engaging components 230 may be separated from each other by breaking frangible points during use or after implantation, as explained above.

Figure 8:
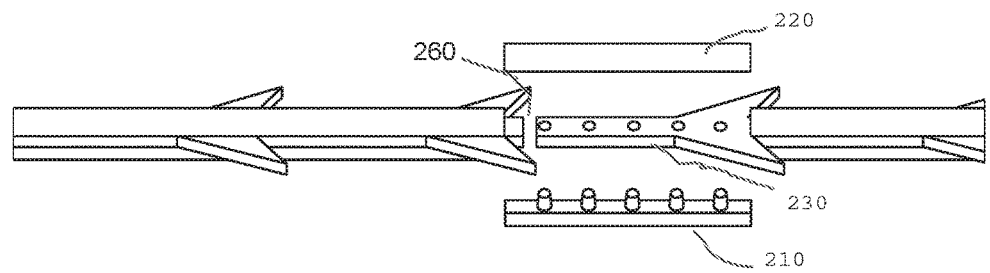
FIG. 8 depicts an embodiment where segments of elongate elastic components are bridging a non-extensible tissue engaging section.

FIG. 8 shows an alternate embodiment similar to FIG. 7, with the difference being that adjacent non-extensible sections 230 are separated from each other by an open space or gap 260 before the first and second elastic components 210, 220 are secured thereto. The first and/or second elastic components 210, 220 may be made of a plurality of individual sections along the axial length of the device 200, or may each individually be a continuous length extending along the full axial length of the device 200 from proximal end to distal end.

The embodiments set forth in FIGS. 7 and 8 are beneficial in that it is easier to set the initial point with zero force. In the embodiment of FIG. 7, before any frangible sections are broken, there is little to no elastic force applying to the target site. Further, it is capable to have variable force setting. That is, the elastic forces depend upon how many frangible sections are broken, giving flexibility for different patient or use requirements.

FIGS. 7 and 8 are intended to depict interconnected, continuous elongate elastic components. It is to be understood that, for illustrative purposes, a removed segment of the elongate elastic components (210, 220) is shown. In actual use, the series of elongate elastic components 210, 220 are preferably continuous, and not removed in segments.

What is claimed is:

1. A tissue fastener having fixed points of tissue attachment comprising:
   (i) a first elongate elastic component comprising an open interior section;
   (ii) a second elongate component that is coaxially disposed within the open interior section, wherein the second elongate component includes two or more elongate sections, wherein each adjacent section is delineated by at least one frangible point;
   wherein each elongate section has one or more tissue anchoring elements, wherein the elasticity of the first elongate elastic component is greater than that of the second elongate component, and wherein the first elongate elastic component is configured to axially stretch the tissue fastener when the at least one frangible point is manually broken.

2. The fastener of claim 1, further comprising an insertion device at a first end.

3. The fastener of claim 1, further comprising an anchoring device at a second end.

4. The fastener of claim 1, further comprising an insertion device at a second end.

5. The fastener of claim 1, wherein each of said tissue anchoring elements extends through the first elongate elastic component such that at least a portion of said tissue anchoring element is exposed on an outer surface of said tissue fastener.

6. The fastener of claim 5, wherein each of said tissue anchoring elements has a pointed tip, and each tissue anchoring element is aligned such that each pointed tip faces in a direction opposite a first end.

7. The fastener of claim 1, wherein said first elongate elastic component comprises a material selected from the group consisting of: silicone, polyurethane, TEO, SEBS, TPV, TPU, COPE, PEBA, and mixtures thereof.

8. The fastener of claim 1, wherein said one or more elongate sections each comprise a material selected from the group consisting of: LDPE, HDPE, LLDPE, UHMPE, PP, nylons, PVDF, PGA, PLA, PLGA, PDS, and mixtures thereof.

9. The fastener of claim 1, wherein said first elongate elastic component is a braided sheath.

10. The fastener of claim 1, wherein said first elongate elastic component and said second elongate component have approximately the same axial length in the absence of axial force enacted thereon.

11. The fastener of claim 1, wherein the entire length of the second elongate component is coaxially disposed within the open interior section.

12. The fastener of claim 1, wherein the one or more tissue anchoring elements of each elongate section face the same direction.

13. The fastener of claim 1, wherein the second elongate component includes between about 5 to about 50 elongate sections.

14. A tissue fastener having fixed points of tissue attachment comprising:
   (i) a first elongate elastic component comprising an open interior section;
   (ii) a second elongate component that is coaxially disposed within the open interior section, wherein the second elongate component includes two or more elongate sections, wherein each adjacent section is delineated by at least one frangible point, wherein the at least one frangible point has a smaller cross-sectional area than the rest of the second elongate component, and wherein the first elongate elastic component is configured to axially stretch the fastener when the at least one frangible point is manually broken;

wherein each elongate section has one or more tissue anchoring elements, and the elasticity of the first elongate component is greater than that of the second elongate component.

15. The fastener of claim 14, wherein each elongate section includes a segment body that is substantially housed within the first elongate elastic component, such that the elongate section is axially aligned with the first elongate elastic component, forming a coaxial arrangement.

16. The fastener of claim 14, wherein the entire length of the second elongate component is coaxially disposed within the open interior section.

17. A tissue fastener having fixed points of tissue attachment comprising:
   (i) a first elongate elastic component comprising an open interior section;
   (ii) a second elongate component that includes first, second, third, and fourth elongate sections, wherein the first, second, third, and fourth elongate sections are each coaxially disposed within the open interior section, wherein the first and second elongate sections are connected at a first frangible point, wherein the second and third elongate sections are connected at a second frangible point, wherein the third and fourth elongate sections are connected at a third frangible point, and wherein the first, second, and third frangible portions are separated by a distance;
   wherein each of the first, second and third elongate sections have one or more tissue anchoring elements, and the elasticity of the first elongate elastic component is greater than that of the second elongate component.

18. The fastener of claim 17, wherein the entire length of the second elongate component is coaxially disposed within the open interior section.

19. The fastener of claim 17, wherein the one or more tissue anchoring elements of the first, second, third, and fourth elongate sections are directed in the same direction.

20. The fastener of claim 17, wherein the first elongate elastic component is configured to axially stretch the fastener when the at least one frangible point is manually broken.

* * * * *